United States Patent [19]

Slifkin

[11] Patent Number: 4,673,639

[45] Date of Patent: Jun. 16, 1987

[54] DRY FORM MICRONITROUS ACID STREPTOCOCCI EXTRACTION-AGGLUTINATION TEST

[75] Inventor: Malcolm Slifkin, Pittsburgh, Pa.

[73] Assignee: Allegheny-Singer Research Institute, Pittsburgh, Pa.

[21] Appl. No.: 773,586

[22] Filed: Sep. 9, 1985

[51] Int. Cl.[4] .............................................. C12Q 1/14
[52] U.S. Cl. ....................................... 435/36; 422/57; 422/61; 435/34; 435/810; 436/519; 436/543
[58] Field of Search ...................... 435/36; 422/57, 58, 422/60, 61; 436/136, 519, 534, 543

[56] References Cited

U.S. PATENT DOCUMENTS

| | | | |
|---|---|---|---|
| 3,666,421 | 5/1972 | Price | 23/253 |
| 3,699,003 | 10/1972 | Kronish | 435/36 |
| 3,790,447 | 2/1974 | Hirata | 435/36 X |
| 4,135,981 | 1/1979 | Simpson | 435/36 X |
| 4,234,316 | 11/1980 | Hevey | 23/230 |
| 4,355,113 | 10/1982 | Mennen | 435/295 |
| 4,387,164 | 6/1983 | Hevey et al. | 436/45 |

OTHER PUBLICATIONS

"Serogrouping of Beta-Hemolytic Streptococci from Throat Swabs with Nitrous Acid Extraction and the Phadebact Streptococcus Test", Journal of Clinical Microbiology, Jan., 1982, pp. 187–189, vol. 15, No. 1, Malcolm Slifkin and Gail M. Gil.

"Identification of Group C Streptococcal Antigen Extracts with Lectin-Bound Polystyrene Particles", Journal of Clinical Microbiology, Jan., 1984, pp. 83–84, vol. 19, No. 1, Malcolm Slifkin and Gail M. Gil.

"Evaluation of the Culturette Brand Ten-Minute Group A Strep ID Technique" Journal of Clinical Microbiology, Jul., 1984, pp. 12–14, vol. 20, No. 1, Malcolm Slifkin and Gail M. Gil.

*Primary Examiner*—Sidney Marantz
*Attorney, Agent, or Firm*—Webb, Burden, Robinson & Webb

[57] ABSTRACT

The present invention is a ready-to-use microtube and method for the simple and accurate identification of beta-hemolytic streptococci from inoculated swabs. Non-volatile reagents are selected and affixed to two separate loci within the microtube by means of a stable, water-soluble or -dispersible binder. At the time of patient examination, the patient site (pharynx, etc.) is swabbed and the swab is placed, tip down, in the prepared microtube. Four to six drops of distilled water are added, the swab is rotated and, after a brief incubation period, an agglutination agent is used to verify the presence or absence of a specific streptococcus group antigen by the presence or absence of a visible agglutination. The test is suitable for use in identifying any streptococcus group which bears antigens susceptible to extraction by nitrous acid, including in particular the clinically significant group A, B, C, F, and G beta-hemolytic streptococci.

14 Claims, No Drawings

4,673,639

DRY FORM MICRONITROUS ACID STREPTOCOCCI EXTRACTION-AGGLUTINATION TEST

FIELD OF THE INVENTION

The present invention relates to ready-to-use microtubes for the onsite extraction and identification of beta-hemolytic streptococci from inoculated swabs.

INTRODUCTION

Group A beta-hemolytic streptococcus is the organism overwhelmingly responsible for the mortality associated with streptococcus-induced endocarditis and glomerulonephritis. As a result, laboratory tests for group A beta-hemolytic streptococci, along with the other beta-hemolytic streptococci, are tools important to health care practitoners and vital to their patients. Accurate diagnosis of beta-hemolytic streptococcal infections is critical, furthermore, not only in the hospital setting (for which laboratory facilities are readily available) but also in family practice and home health care settings for which diagnostic laboratories are less accessible. Family practitioners, as a result, frequently must forward swabs or cultures to the laboratory by mail or courier, and must thereafter either delay treatment entirely until diagnostic tests are complete or prescribe initial treatment without benefit of the results. Neither alternative enables satisfactory patient care.

BACKGROUND OF THE INVENTION

In response to this need, a number of test kits have been developed to enable onsite identification of group A and other beta-hemolytic streptococci in, for example, an office or clinic setting. One of these test kits was evaluated in the article by Slifkin, M. and Gil, G., "Evaluation of the Culturette Brand Ten-Minute Group A ID Technique," *J. Clin. Microbiology,* Vol. 20, pp. 12-14, 1984. In this study, the latex reagent kit "Culturette Brand Ten-Minute Group A Strep ID" (Marion Scientific, Division of Marion Laboratories, Inc., Kansas City, Mo.) was evaluated for sensitivity, accuracy and suitability for the direct serogrouping of group A streptococci from throat swabs as compared with standard throat swab cultures.

In the Culturette test, a pharyngeal culture was obtained by rubbing a swab over the patient's throat. The swab was placed in a microtube subsequent to the dropwise addition of two extraction agents to the tube. The swab was then rolled against the wall of the microtube to express liquid from the swab into the microtube. After the swab was incubated for five minutes at room temperature, two drops of a third extraction reagent were added. The swab was rolled and pressed against the microtube and then incubated for an additional ten minutes.

The swab, after having been placed in the microtube and extracted, was briefly rolled—to release extraction fluid from the swab—onto two circular areas of the glass slide provided in the kit. One drop of the latex group A Strep ID kit was next added to one of these circular areas, and one drop of the negative control reagent was added to the other circular area. The slide was then rocked back and forth by hand for two to three minutes and examined for agglutination of the latex particles. A positive control reagent was also available in the kit and was employed on a daily basis to test the activity of the group A detection agent.

This study by Slifkin and Gil, although directed generally to the sensitivity and accuracy of the test kit, also illustrates the inconvenient procedures inherent in liquid-reagent test kits. Reagents are added dropwise, and the practitioner can easily dispense too little or too much of any of four reagents. Moreover, two sequential incubations plus a two or three minute rocking period contribute to an overall procedure which is awkward and time-consuming, not to mention potentially inaccurate in the event of procedural error.

Without doubt, busy practitioners need a test for the onsite identification of beta-hemolytic streptococci which is simple and reliable and yet requires only a few minutes of minimized attention.

BRIEF DESCRIPTION OF THE INVENTION

In order to meet this need, the present invention is a ready-to-use microtube and method for the simple and accurate identification of betahemolytic streptococci from inoculated swabs. Non-volatile reagents are selected and affixed to two separate loci within the microtube by means of a stable, water-soluble carrier. At the time of patient examination, the patient site (pharynx, etc.) is swabbed and the swab is placed, tip down, in the prepared microtube. Four to six drops of distilled water are added, the swab is rotated and, after a brief incubation period, an agglutination agent is used to verify the presence or absence of a specific streptococcus group antigen by the presence or absence of a visible agglutination. The test is suitable for use in identifying any streptococcus group which bears antigens susceptible to extraction by nitrous acid, including in particular the clinically significant group A, B, C, F, and G beta-hemolytic streptococci.

DETAILED DESCRIPTION OF THE INVENTION

The present invention is a ready-to-use test microtube and method for Dry Form Micronitrous Acid Streptococci Extraction-Agglutination which provides not only rapid test results but also accuracy comparable with known methods of nitrous acid extraction.

In general terms, the present invention is an improvement in the identification of organisms by their antigens. Antigenic macromolecules (i.e., polysaccharides, polypeptides, etc.), which append from the outer surface of bacterial cell walls, are specific to the bacterial species, type, group of strain. When these antigenic macromolecules are exposed to the corresponding specific antibodies, the antigens and antibodies bind together to form an insoluble precipitin. Furthermore, if the antibody is present on a carrier, such as a nonviable bacterium or another small particle, even a relatively small number of antigens and antibodies will agglutinate with the particles or bacteria to yield an agglutination visible without magnification. Accordingly, an unknown bacterial organism will be identified by isolating or extracting its antigens and exposing them to antibodies of a known specificity, one at a time, until the formation of an agglutinate identifies the organism as that for which the agglutinating antibody is specific. Moreover, the presence or absence of a particular bacterial organism in a culture or swab may be verified by a single exposure to the corresponding antibody.

The improvement of the present invention embodies a prepared microtube and method for swift extraction and agglutination of antigens from inoculated swabs. The prepared microtubes carry accurate amounts of the necessary test reagents for nitrous acid extraction of beta-hemolytic streptococcus strains. Non-volatile reagents are selected and affixed to two separate loci within the microtube by means of a stable, water-soluble carrier. At the time of patient examination, a fiber-tipped swab is rubbed over the pharynx or other site of suspected infection and is placed, tip down, in a prepared microtube. Four to six drops of distilled water are added to the microtube, the swab is rotated and, after a five minute incubation period, the presence or absence of a specific beta-hemolytic streptococcus group is detected with an antibody-containing group specific agglutination agent. The microtube and method, described in detail below, are suitable for use in identifying any beta-hemolytic streptococcus group which bears antigens susceptible to extraction by nitrous acid, including in particular the clinically significant group A, B, C, F and G beta-hemolytic streptococci.

It is well known that nitrous acid is a chemically unstable compound. Nitrous acid is known only in solution, yet quickly forms nitric acid and nitric oxide in the presence of water. As a result, polysaccharides have conventionally been extracted by the nitrous acid formed from the reaction between an inorganic nitrite and an aqueous acid, with sodium nitrite and glacial acetic acid as the reactants of choice. As the nitrous acid contacts the exterior cell walls of the bacterium, the group antigen is released into solution with its antibody specific reactivity intact. When the extracted group antigen is contacted with an agglutination agent which contains the corresponding antibody, a visible agglutinate results.

The present invention is a prepared microtube for and a method of nitrous acid extraction of group polysaccharides which eliminate the need for measurement or delivery of the nitrous acid producing reactants into a suitable laboratory vessel. Instead, the present invention provides a prepared microtube which generates nitrous acid upon the simple addition of distilled water. The prepared microtube thus enables extraction of the group polysaccharide from inoculated swabs simply by placing the swab tip down into the microtube, adding a few drops of distilled water, rotating and squeezing the tip of the swab and allowing a brief (e.g., five minute) incubation period.

The prepared microtubes of the present invention are prepared by affixing, at separate loci within the microtube and by means of a suitable carrier, the two reactants which combine to produce nitrous acid. Reagents which are nonvolatile and compositionally stable at ambient temperatures (i.e., 15-°30° C.) are required. Accordingly, the conventional glacial acetic acid reactant of typical nitrous acid extractions is unsuitable for incorporation in the prepared vial inasmuch as it has a boiling point of 117.9° C. and commensurate high volatility at ambient temperatures.

The acid reactant chosen for affixing to the subject microtubes is, therefore, one of the nonvolatile organic acids. Suitable nonvolatile organic acids include citric (2-hydroxy-1,2,3,-propane tricarboxylic acid), oxalic (ethanedioic), malonic (propanedioic), succinic (butanedioic), glutaric (pentanedioic) and adipic (hexanedioic) acids. Other mono-, di- and tricarboxylic acids which are substantially nonvolatile at ambient conditions are suitable for incorporation in the present microtube as long as they react with inorganic nitrites to form nitrous acid. Due to its low cost and wide availability, citric acid is the preferred nonvolatile organic acid for the purpose of the present invention.

The use of nonvolatile mono-, di- or tri-carboxylic acid as the organic acid of the present invention provides an additional advantage over those methods of nitrous acid extraction which incorporate an acetic acid reactant. Whereas unreacted acetic acid present in the extraction admixture *must* be neutralized with a buffer before the addition of the agglutination agent (in order to prevent "false positive" clumping), the present method requires no neutralization step or reagent in order to yield consistently accurate results. Accordingly, the present microtube and method provide not only for a convenient prepared test receptacle but also completely eliminate the step of buffering or neutralizing the extraction admixture, prior to the addition of the agglutination agent, as required by the prior art.

The inorganic nitrite chosen for incorporation in the subject microtube is selected from the group consisting of the inorganic nitrites of Na, Li, K, Ca, Sr, Ba and Ag. Although sodium nitrite is the preferred nitrite for the purpose of the present microtube and method all of the inorganic nitrites are nonvolatile in solution and are stable compounds when dry.

One at a time, the inorganic nitrite and the organic acid reactants are affixed to two separate loci within the microtube by means of a water-soluble or -dispersible carrier or binder. The binder may be selected from the group consisting of dextran, polyacrylamide, polyacrylic acid, polyvinyl alcohol, polyethylene glycol, polyethylene oxide, polyvinyl pyrrolidone, guar gum, carboxymethylcellulose, hydroxyethyl cellulose, methyl cellulose, algin, carrageenan, xanthan gum, starch, copolymers of maleic anhydride with various vinyl monomers as described, for example, in U.S. Pat. No. 2,074,398, and the like. In addition, binders of non-polymeric, relatively low molecular weight compounds may be used including sorbitol, potassium or sodium tartrate, mannose and sucrose. Binders or carriers may contain one, two or more different materials and may incorporate plasticizers, surfactants and other additives inert to the reaction. The preferred binders are carboxymethylcellulose, polyvinyl alcohol, polyethylene glycol, hydroxyethyl cellulose, methyl cellulose, carrageenan and xantham gum. The most preferred binder, due to its wide availability, high performance and low cost, is carboxymethylcellulose.

Ordinarily, the organic acid or inorganic nitrite reagent is admixed with the selected binder in aqueous solution for dispersion before application to the microtube. The reagent/binder system is then deposited on a locus of a microtube and the water is evaporated therefrom to yield a "dry form" reagent. Generally, from 1 to 10% of the binder should be dissolved or dispersed in the aqueous reagent to yield optimal binding of the reagent upon evaporation of the reagent-/binder solution within the microtube. Binder amounts in excess of 10% continue to provide good fixation of the reagent to the microtube, but require excessive agitation at the time of patient examination to release the reactant bound therein.

Incorporation of correct amounts of the reactants in the microtube is important to the present invention. The inorganic nitrite should be added to the microtube in an amount equivalent to between about one to eight drops of a 4 M. solution of the nitrite. The organic acid should be added to the microtube in an amount stoichiometrically equivalent to between about one to eight drops of 5% citric acid. (For the purpose of the present disclosure, the drop equals approximately 0.1 ml.) Lesser or greater amounts of the two reactants yield inferior antigen extraction.

Although each reagent/binder admixture must be affixed to a separate locus within the microtube, the reagents may be positioned at any two separate loci therein. A particularly convenient method of producing the prepared microtube, however, includes the deposition and evaporation of one reagent/binder preparation to the bottom of the microtube as it stands upright, followed by deposition and evaporation of the second reagent/binder preparation to the wall of the microtube as it lies on its side. This technique is particularly effective, during mass production of the microtubes, to prevent confluence of the deposited reagents before evaporation is complete.

The microtubes of the present invention may have a wide range of shapes and sizes and may be manufactured from a wide variety of materials known in the art. The microtubes are generally "micro," i.e., smaller than a conventional laboratory tube, in order to accommodate an extraction procedure which takes place within a few drops of fluid surrounding a small swab tip. For this reason, the microtubes generally are tubes having a height between 1.5 and 3 cm. and a diameter between 0.5 and 1.5 cm. More preferably, the microtube has a conical tip but also has a means, such as an annular base, which allows the microtube to stand upright on a flat surface. By the use of the term microtube, however, applicant specifies only the receptacle of the preferred embodiment of his invention; a wide variety of laboratory vessels constitute suitable receptacles for the purpose of this application, including tubes, vials and wells.

The swabs of the present test kit may be any pharyngeal or other swab known in the art, but preferably the present swabs have flexible shanks and fibrous tips inert to nitrous acid. The fibrous tips preferably comprise a tuft of a non-woven fiber and more preferably consist of a tuft of a chemically resistant synthetic fiber such as Dacron ® polyester. The fibrous tip is attached to the shaft of the swab by means known in the art.

In order to carry out the present method, the health care practitioner proceeds as follows. A swab is rubbed vigorously over the site suspected of infection, including the pharynx, urogenital regions, etc. The swab is then placed, tip down, into a microtube prepared with the dry form inorganic nitrite and non-volatile organic acid reagents as described above. Four to six drops of distilled water are added to the microtube, and the swab is rotated or otherwise agitated within the microtube in order to release and to admix the nitrous acid reactants. The microtube with the swab therein is then permitted in incubate for a short time. The swab is subsequently rolled and squeezed against the sides of the microtube in order to deliver the antigen extract back into the tube.

The short incubation of the microtube requires from about three to seven minutes and usually about five minutes, at ambient conditions. The incubation period provides time for the nitrous acid to act upon and extract the streptococcal antigens but, because the nitrous acid extraction proceeds rapidly in the presence of the disclosed amounts of reactants, the incubation time is swift and presents no inconvenience to the clinician.

After incubation, one drop of the nitrous acid antigen extract is removed from the microtube and placed on a clean laboratory slide. The drop may be removed with a clean or sterile pipette or may be dropped directly from the swab. One drop of an agglutination agent is added to the drop of antigen extract on the slide and the admixture is observed for agglutination. Because the present method produces a highly visible agglutinate within about one to four minutes after contact of the extracted antigen with the corresponding antibody present in the agglutination reagent the slide need not be rocked back and forth to enhance agglutination and does not require examination under magnification. The presence of an agglutinate indicates, of course, the presence of the antigen which corresponds to the specific agglutination agent used.

The agglutination agents for the purpose of the present invention may be either latex or coagglutination preparations. Latex agglutination preparations contain known group specific antibodies attached to latex particles, such as polystyrene particles and the like. Coagglutination preparations are suspensions of non-viable bacterial particles, such as *Staphylococcus aureus*, in which the non-viable bacteria carry the known, group-specific antibodies. The preparations may be made by attaching antibodies to polystyrene spheres (CX-Covasphere; Covalent Technology Corp., Ann Arbor, Mich.) or to the nonvirulent *Staphylococcus aureus* by means known in the art. Because such preparations are available commercially, however, the agglutination agent may be obtained directly from a supplier. For example, Pharmacia Diagnostics manufactures and distributes coagglutination agents specific to the clinically significant group A, B, C, F, and G beta-hemolytic streptococci, along with numerous others.

In the alternate embodiment of the invention, only one of the two nitrous acid generating reactants is affixed to the microtube in advance of use. More particularly, the microtube may be prepared with either the inorganic nitrite or the organic acid. Depending upon which one of the two reactants is affixed to the prepared tube, formation of nitrous acid requires only the dropwise addition of the other agent. Because the overall simplicity of the present prepared microtube and method, in which neither aqueous reactants nor buffer are necessary as is the case in other commercially available streptococcus tests, dropwise addition of a single reagent does not overburden the health care professional. After admixture, extraction, incubation and delivery of the extract from the swab into the tube, the agglutination step proceeds as described above.

It is preferred, although not strictly necessary, that the equipment used in the preparation and execution of the present invention be sterile. Scrupulously clean equipment may be substituted for sterile equipment, however, inasmuch as groupable beta-hemolytic streptococci thrive generally only in vivo or on blood agar, and ordinarily do not survive soap and hot water. Nonetheless, the use of sterile microtubes, slides, pipettes, etc. is preferred in order to maximize the accuracy of the present method.

The invention will be more fully described with reference to the specific examples herein set forth.

EXAMPLE I

A 4 M. solution of sodium nitrite was admixed with carboxymethylcellulose to yield a 1% solution of carboxymethylcellulose in the aqueous sodium nitrite. In a separate laboratory vessel, 5% aqueous citric acid was admixed with carboxymethylcellulose to yield a 1% solution of carboxymethylcellulose in the citric acid.

Each solution was separately charged to a sterile laboratory storage vessel and the vessels were tightly capped.

Six sterile freestanding plastic microtubes, measuring 2 cm. in height and 0.75 cm. in diamter, were placed on their sides on a sterile laboratory rack. A 1 ml. pipette was filled with the citric acid/carboxymethylcellulose solution, and three drops of the solution were deposited on the side of each microtube. The microtubes were air dried. The six microtubes were placed upright and three drops of the sodium nitrite/carboxymethylcellulose solution was added to a conical tip in the bottom of each microtube and the microtubes were air dried.

At the time of patient examination, a throat swab was inoculated from the pharynx of the patient and was immediately deposited, tip down, into the microtube. Six drops of distilled water were added to the tube from a plastic squeeze bottle. The swab was rotated within the microtube and the two dried reactants dissolved and formed nitrous acid in aqueous solution. The microtube was left undisturbed for a five minute incubation period to ensure complete extraction of any beta-hemolytic streptococcal antigens present in the swab. After five minutes, the swab was rotated and squeezed against the sides of the microtube to squeeze the antigen extract from the swab back into the microtube.

One drop of the extract in the microtube was removed with a micropipette and deposited on a sterile microscope slide. One drop of the Phadebact streptococcus test reagent specific for group A (Pharmacia Diagnostics) was added directly to the drop of extract on the slide. The slide was permitted to remain undisturbed for one minute, after which a visible agglutinate indicated the presence of group A beta-hemolytic streptococcus on the swab inoculated from the site of suspected infection.

EXAMPLE II

The microtubes were prepared and the nitrous acid extraction method proceeded as in Example 1. After the swab was rolled and squeezed against the sides of the microtube in order to express the nitrous acid extract therefrom, the extract was vacuum aspirated into a 1 ml. pipette. One drop of the extract was deposited into each of 5 wells on a plastic laboratory substrate. Each drop of extract was then combined with 1 drop each of 5 different agglutination agents. The 5 agglutination agents were specific for group A, B, C, F, and G beta-hemolytic streptococci. After ninety seconds, each admixture in each of the 5 wells was observed for the presence or absence of agglutinate.

The present test kit and method affords a convenient and accurate onsite streptococcus identification test for health care professionals because the partially or completely prepared microtubes require only the addition of a few drops of distilled water—or a few drops of a single reagent—and the insertion of a swab. The reagents affixed to the microtube contribute not only the accuracy of the antigen extraction but contribute markedly to the convenience of the test and method to busy practitioners who cannot be concerned with accurate reagent delivery or long incubation periods.

Although the invention has been described with reference to particular processes and particular materials, the invention is to be limited only insofar as is set forth in the accompanying claims.

I claim:

1. A test device for detecting streptococci comprising
   (a) a test vial having sodium nitrite affixed therein by means of a binder,
   (b) a container holding citric acid which when added to the test vial will react with the sodium nitrite to form nitrous acid; and
   (c) a swab capable of being inserted in the vial after being inoculated with an infected region suspected of including streptococcal antigens.

2. A test device for detecting streptococci comprising
   (a) a test vial having an inorganic nitrite affixed therein by means of a binder,
   (b) a container holding a nonvolatile organic acid which when added to the test vial will react with the inorganic nitrite to form nitrous acid; and
   (c) a swab capable of being inserted in the vial after being inoculated with an infected region suspected of including streptococcal antigens.

3. The test device of claim 2 wherein said inorganic nitrite is selected from the group consisting of inorganic nitrites of Na, Li, K, Ca, Sr, Ba and Ag.

4. The test device of claim 2 wherein said organic acid is selected from the group consisting of citric acid, oxalic acid, malonic acid, succinic acid, glutaric acid and adipic acid.

5. The test device of claim 2 wherein said binder is selected from the group consisting of carboxymethylcellulose, polyvinyl alcohol, polyethylene glycol, hydroxyethyl cellulose, methyl cellulose, carrageenan and xanthan gum.

6. A test device for detecting streptococci comprising
   (a) a test vial having a first reactant capable of producing nitrous acid affixed therein by means of a binder,
   (b) a source of a second reactant which when added in aqueous form to the test vial will produce nitrous acid; and
   (c) means for extracting a specimen from an infected area suspected of containing streptococcal antigen said means being capable of inserting the specimen into the test vial.

7. A test vial for use in determining the presence of streptococcal antigens said vial having affixed thereto by means of a binder at least one reactant capable of producing nitrous acid when an aqueous solution of a second nitrous acid producing agent is added said vial being adapted to receive a swab inoculated with an infected area suspected of including steptococcal antigen.

8. A test vial for use in determining the presence of streptococcal antigens said vial having two reactants capable of reacting to produce nitrous acid affixed to the vial at separate locations by means of a binder said reactants being capable of mixing and producing nitrous acid when distilled water is added to the vial said vial being adapted to receive a swab inoculated with an infected area suspected of including streptococcal antigen.

9. A test vial of claim 8 wherein said two nitrous acid producing reactants further comprise an inorganic nitrite and a nonvolatile organic acid, each of which is affixed by said binder to one of two separate loci within said receptable.

10. A method of detecting streptococci comprising
    (a) adding one nitrous acid producing reactant in aqueous form to a vial having a second nitrous acid producing reactant affixed thereto by means of a binder to form nitrous acid, (b) inoculating a swab with an infected region suspected of including streptococcal antigens and inserting said swab into said vial after formation of nitrous acid therein, (c) inoculating said receptacle to extract streptococcal antigen present in the swab; and (d) identifying the presence of extracted antigen with an agglutination agent.

11. The method of claim 10 wherein the nitrous acid producing reactant affixed to the vial is selected from the group consisting of inorganic nitrites of Na, Li, K, Ca, Sr, Ba and Ag.

12. The method of claim 10 in which the nitrous acid producing reactant added in aqueous form is selected from the group consisting of citric acid, oxalic acid, malonic acid, succinic acid, glutaric acid and adipic acid.

13. A method of detecting streptococci comprising
(a) adding an aqueous solution of citric acid to a test vial having sodium nitrite affixed thereto by means of a binder to form nitrous acid, (b) inoculating a swab with an infected region suspected of including streptococcal antigens and inserting said swab into said vial after formation of nitrous acid therein, (c) inoculating said receptacle to extract streptococcal antigen present in the swab; and (d) identifying the presence of extracted antigen with an agglutination agent.

14. A method of detecting streptococci comprising
(a) adding distilled water to a test vial having two nitrous acid producing reactants affixed to the vial at separate locations by means of a binder thereby producing nitrous acid in the vial, (b) inoculating a swab with an infected region suspected of including streptococcal antigens and inserting said swab into said vial after formation of nitrous acid therein, (c) inoculating said receptacle to extract streptococcal antigen present in the swab; and (d) identifying the presence of extracted antigen with an agglutination agent.

* * * * *

UNITED STATES PATENT AND TRADEMARK OFFICE
CERTIFICATE OF CORRECTION

PATENT NO. : 4,673,639

DATED : June 16, 1987

INVENTOR(S) : Malcolm Slifkin

It is certified that error appears in the above-identified patent and that said Letters Patent is hereby corrected as shown below:

Column 2 Line 21 "betahemolytic" should read --beta-hemolytic--.

Column 2 Line 50 "of" should read --or--.

Column 2 Line 59 "will" should read --may--.

Column 5 Line 3 "the" should read --one--.

Claim 9 - Column 8 Line 63 "receptable" should read --vial--.
example, Application Page 7 Line 29.)

Claim 10 - Column 9 Line 5 "inoculating" should read --incubating-- and "receptacle" should read --vial--.

Claim 13 - Column 10 Line 5 "inoculating" should read --incubating-- and "receptacle" should read --vial--.

UNITED STATES PATENT AND TRADEMARK OFFICE
CERTIFICATE OF CORRECTION

PATENT NO. : 4,673,639

DATED : June 16, 1987

INVENTOR(S) : Malcolm Slifkin

It is certified that error appears in the above-identified patent and that said Letters Patent is hereby corrected as shown below:

Claim 14 - Column 10 Line 18 "inoculating" should read --incubating-- and "receptacle" should read --vial--.

Signed and Sealed this

Twenty-second Day of March, 1988

Attest:

DONALD J. QUIGG

Attesting Officer      Commissioner of Patents and Trademarks